United States Patent
Wright et al.

(10) Patent No.: US 6,457,362 B1
(45) Date of Patent: Oct. 1, 2002

(54) METHOD AND APPARATUS FOR DIAGNOSING AND REMEDIATING LANGUAGE-BASED LEARNING IMPAIRMENTS

(75) Inventors: Beverly A. Wright, Evanston, IL (US); Michael M. Merzenich, Pacifica, CA (US); Srikantan Nagarajan; Athanassios Protopapas, both of San Francisco, CA (US)

(73) Assignee: Scientific Learning Corporation, Oakland, CA (US)

( * ) Notice: Subject to any disclaimer, the term of this patent is extended or adjusted under 35 U.S.C. 154(b) by 0 days.

(21) Appl. No.: 10/027,518

(22) Filed: Dec. 20, 2001

Related U.S. Application Data (62) Division of application No. 09/617,585, filed on Jul. 18, 2000, which is a division of application No. 08/852,651, filed on May 7, 1997, now Pat. No. 6,109,107.

(51) Int. Cl.[7] ................................................. A61B 5/12

(52) U.S. Cl. ........................................ 73/585; 600/559

(58) Field of Search ........................... 73/585; 600/559; 434/185, 156, 118, 169

(56) References Cited

U.S. PATENT DOCUMENTS

| | | |
|---|---|---|
| 3,721,764 A | 3/1973 | Dunn |
| 3,816,664 A | 6/1974 | Koch |
| 3,906,158 A | 9/1975 | Lake |
| 3,920,903 A | 11/1975 | Beller |
| 4,010,557 A | 3/1977 | Martin et al. |
| 4,128,737 A | 12/1978 | Dorais |
| 4,224,468 A | 9/1980 | Calder, Jr. |
| 4,327,252 A | 4/1982 | Tomatis |

(List continued on next page.)

OTHER PUBLICATIONS

*Proceedings of the National Conference on Learning Disabilities.*, Bethesda, MD, Jan. 12–13, 1987 (York, Parkton, MD, 1988).

Aaron, P.G., et al., "Is There A Thing Called Dyslexia," *Annals of Dyslexia, 38:*33–49 (1988).

Alexander, A., et al., "Phonological Awareness Training and Remediation of Analytic Decoding Deficits in a Group of Severe Dyslexics," *Annals of Dyslexia,* 41:193–206 (1991).

Aram, D.M., et al., "Patterns of Language Behavior in Children With Developmental Language Disorders," *Journal of Speech and Hearing Research, 18:*229–241 (1975).

Berkell, Dianne E. et al., "Auditory Integration Training for Individuals with Autism," *Education and Training in Mental Retardation and Developmental Disabilities* v31, n1 66–70 (1996).

Bérard, G., M.D., "Hearing Equals Behavior," *Keats Publishing, Inc.,* 77–93 (1993).

Bradley, L., et al., "Difficulties in auditory organisation as a possible cause of reading backwardness," *Naure, 271:*746–747 (1978).

Burne, J., "Crazy sounds to soothe a garbled world," *The Independent II,* 24 (1994).

Carlyon, R.P. "Changes in the masked thresholds of brief tones produced by prior bursts of noise," *Hearing Research, 41:*223–236 (1989).

(List continued on next page.)

*Primary Examiner*—Hezron Williams
*Assistant Examiner*—Rose M. Miller
(74) *Attorney, Agent, or Firm*—Morrison & Foerster LLP (57) ABSTRACT

The present invention provides an improved method and apparatus for the identification and treatment of language perception problems in specific language impaired (SLI) individuals. The invention provides a method and apparatus for screening individuals for SLI and training individuals who suffer from SLI to remediate the effects of the impairment by using the spectral content of interfering sound stimuli and the temporal ordering or direction of the interference between the stimuli.

19 Claims, 11 Drawing Sheets

U.S. PATENT DOCUMENTS

| | | |
|---|---|---|
| 4,390,748 A | 6/1983 | Zwicker |
| 4,464,119 A | 8/1984 | Vildgrube et al. |
| 4,515,169 A | 5/1985 | Ward |
| 4,586,905 A | 5/1986 | Groff |
| 4,641,343 A | 2/1987 | Holland et al. |
| 4,696,042 A | 9/1987 | Goudie |
| 4,708,657 A | 11/1987 | Beller et al. |
| 4,736,429 A | 4/1988 | Niyada et al. |
| 4,741,037 A | 4/1988 | Goldstern |
| 4,799,261 A | 1/1989 | Lin et al. |
| 4,821,325 A | 4/1989 | Martin et al. |
| 4,852,168 A | 7/1989 | Sprague |
| 4,852,170 A | 7/1989 | Bordeaux |
| 4,884,972 A | 12/1989 | Gasper |
| 4,895,519 A | 1/1990 | Beller et al. |
| 4,980,917 A | 12/1990 | Hutchins |
| 5,010,495 A | 4/1991 | Willets |
| 5,056,143 A | 10/1991 | Taguchi |
| 5,119,826 A | 6/1992 | Baart de la Faille |
| 5,123,048 A | 6/1992 | Miyamae et al. |
| 5,143,081 A | 9/1992 | Young et al. |
| 5,215,468 A | 6/1993 | Lauffer et al. |
| 5,285,498 A | 2/1994 | Johnston |
| 5,289,521 A | 2/1994 | Coleman et al. |
| 5,295,223 A | 3/1994 | Saito |
| 5,302,132 A | 4/1994 | Corder |
| 5,305,420 A | 4/1994 | Nakamura et al. |
| 5,340,316 A | 8/1994 | Javkin et al. |
| 5,341,432 A | 8/1994 | Suzuki et al. |
| 5,393,236 A | 2/1995 | Blackmer et al. |
| 5,421,731 A | 6/1995 | Walker |
| 5,429,513 A | 7/1995 | Diaz-Plaza |
| 5,487,671 A | 1/1996 | Shpiro et al. |
| 5,517,595 A | 5/1996 | Kleijn |
| 5,540,589 A | 7/1996 | Waters |
| 5,573,403 A | 11/1996 | Beller et al. |
| 5,813,862 A | 9/1998 | Merzenich et al. |
| 5,927,988 A * | 7/1999 | Jenkins et al. .............. 434/116 |
| 6,071,123 A | 6/2000 | Tallal et al. |
| 6,123,548 A | 9/2000 | Tallal et al. |
| 6,210,166 B1 * | 4/2001 | Jenkins et al. .............. 434/118 |

OTHER PUBLICATIONS

Catts, H.W., "The Relationship Between Speech–Language Impairments and Reading Disabilities," *Journal of Speech and Hearing Research* 36:948–958 (1993).

Elliott, L.L., et al., "Fine–Grained Auditory Discrimination in Normal Children and Children with Language–Learning Problems" *Journal of Speech and hearing Research*, 32:112–119 (1989).

Farmer, M.E. et al., "The evidence for a temporal processing deficity linked to dyslexia: A review," *Psychonomic Bulletin & Review*, 2:460–493 (1995).

Fastl, H., "Temporal masking effects: II.," *Acustica*, 36:317–330 (1976).

Frumkin, B., et al., "Perception of Vowels and Consonant–Vowels of Varying Duration in Language Impaired Children," *Neuropsychologia* 18:443–454 (1980).

Gauger, L.M., et al., "Brain Morphology in Children With Specific Language Impairment," *Journal of Speech, Language, and Hearing Research*, 40:1272–1284 (1997).

Green, D.M. "Stimulus selection in adaptive psychophysical procedures," *J. Acoust. Soc. Am.*, 87:2662–2674 (1990).

Kraus, N., et al., "Auditory Neurophysiologic Responses and Discrimination Deficits in Children with Learning Problems," *Science,273*:971–973 (1996).

Lubert, N., "Auditory Perceptual Impairments in Children with Specific Language Disorders: A Review of the Literature," *Journal of Speech and Hearing Disorders, 46*:3–9 (1981).

Mehler, J., et al., "Understanding Compressed Sentences: The Role of Rhythm and Meaning," *Annals of the New York Academy of Sciences,* 682:272–282 (1993).

Merzenich, M.M., et al., "Temporal Processing Deficits of Language–Learning Impaired Children Ameliorated by Training," *Science, 271*:77–81 (1996).

Moore, B.C.J., et al., "The temporal course of masking and the auditory filter shape,"*J. Acoust. Soc. Am., 81*:1873–1880 (1987).

Patterson, R.D., et al., "Auditory filters and excitation patterns as representations of frequency resolution," *Frequency Selectivity in Hearing,* (ed. Moore, B.C.J.) 123–176 (Academic Press, NY. 1986).

Patterson, R.D., et al., "The deterioration of hearing with age: Frequency selectivity, the critical ratio, the audiogram, and speech threshold," *J. Acoust. Soc. Am., 72*:1788–1803 (1982).

Rimland, B., Ph.D., "Brief Report: A Pilot Study of Auditory Integration Training in Autism" *Journal of Autism and Developmental Disorders,* v25, n1, pp. 61–70 (1995).

Rimland, B., Ph.D., "Summaries of Research on Auditory Integration Training (1993–1995: 11 Studies)," *Autism Research Institute.*

Soderquist, A.A., et al., "Backward, Simultaneous and Forward Masking as a Function of Signal Delay and Frequency," *The Journal of Auditory Research, 21*:227–245 (1981).

Studdert–Kennedy, M., et al., "Auditory temporal perception deficits in the reading–impaired: A critical review of the evidence," *Psychonomic Bulletin & Review 2:* 508–514 (1995).

Tallal, P., et al., "Defects of Non–Verbal Auditory Perception in Children with Developmental Aphasia," *Nature, 241*:486–469 (1973).

Tallal, P., et al., "Developmental Aphasia: Impaired Rate of Non–Verbal Processing as a Function of Sensory Modality," *Neuropsychologia, 11*:389–398 (1973).

Tallal, P., et al., "Developmental Aphasia: Rate of Auditory Processing and Selective Impairment of Consonant Perception," *Neuropsychologia, 12*:83–93 (1974).

Tallal, P., et al., "Developmental Aphasia: The Perception of Brief Vowels and Extended Stop Consonants," *Neuropsychologia, 13*:69–74 (1975).

Tallal, P., et al., "Language Comprehension in Language–Learning Impaired Children Improved with Acoustically Modified Speech," *Science,* 271:81 (1996).

Tallal, P., et al., "Neurobiological Basis of Speech: A Case for the Preeminance of Temporal Processing," *Annals of the New York Academy of Sciences,* 682:27–47 (1993).

Vellutino, F.R., et al., "Has the Perceptual Deficit Hypothesis Led Us Astray?," *Journal of Learning Disabilities, 10, n.6*:375–385 (1977).

Wagenaar, W.A., "Note On The Construction Of Digram–Balanced Latin Squares," *Psychological Bulletin, 72,n.6*:384–386 (1969).

PCT Written Opinion dated Sep. 18, 1997.

PCT Search Report dated May 18, 1996 which relates to International Application No. PCT/US95/15204.

Alexander, D.B., et al., "Decelerated Synthesized Speech as a Means of Shaping Speed of Auditory Processing of Children With Delayed Language", *Perceptural and Motor Skills, 55,* 783–792, (1982).

Berninger V. W. et al., "Early Intervention for Reading Disabilities: Teaching the Alphabet Principle in a Connectionist Framework", *J. of Learning Disabilities vol. 23, No. 6,* 491–503 (Nov./Dec. 1999).

Bradley, L., et al., "Categorizing sounds and learning to read–a causal connection" Dept. of experimental Psychology, Univ. of Oxford, UK, *Nature vol. 301,* 419–421, (Feb. 3, 1983).

Hurford D. P., "Training Phonemic Segmentation Ability with a Phonemic Discrimination Intervention in Second– and Third–Grade Children with Reading Disabilities", *J. of Learning Disabilities,* vol. 23, No. 9, 564–569, Nov. 1990.

Hurford D. P., et al., "Assessment and Remediation of a Phonemic Discrimination Deficit in Reading Disabled Second and Fourth Graders", *J. of Exper. Child Psychology 50,* 396–415, (1990).

Karma K., et al., "Training in auditory/visual pattern matching improves basic reading skills in reading–impaired children", Nature Editorial, 3 pgs., Aug. 2000.

Lovett M. W. "Can Dyslexia Be Treated? Treatment–Specific and Greralized Treatment Effects in Dyslexic Children's Response to Remediation", *Brain and Language 37,* 90–121, (1989).

McReynolds L. V., "Operant Conditioning for Investigating Speech Sound Discrimination in Aphasic Children", *J. of Speech and Hearing Research 9,* 519–528, (1966).

McReynolds L. V., "Verbal Sequence Discrimination Training for Language Impaired Children", *J. of Speech and Hearing Disorders, 3,* 429–257, (no date).

Robin, D. A., et al., "Auditory Temporal Pattern Learning in Children with Speech and Language Impairments", *Brain and Language 36,* 604–613, (1989).

Tomblin Bruce J. et al., "The Contribution of Perceptual Learning to Performance on the Repetition Task", *J. of Speech and Hearing Research* vol. 26, 369–372, (Sep. 1983).

Weismer S. E., et al., "Lexical Learning by Children With Specific Language Impairment: Effects of Linquistic Input Presented at Varying Speaking Rates", *J. of Speech and Hearing Research* vol. 39, 177–190, (Feb. 1996).

* cited by examiner

COLLECT RESPONSES

Wait for Key
or Mouse
Button Input

Determine Whether
Input is Correct
or Incorrect

Return

METHOD AND APPARATUS FOR DIAGNOSING AND REMEDIATING LANGUAGE-BASED LEARNING IMPAIRMENTS

This application is a divisional of U.S. patent application Ser. No. 09/617,585 filed Jul. 18, 2000, which is a divisional of U.S. patent application Ser. No. 08/852,651 filed May 7, 1997, which issued as U.S. Pat. No. 6,109,107 on Aug. 29, 2000.

BACKGROUND OF THE INVENTION

Research suggests that between three and six percent of individuals who are otherwise unimpaired have extreme difficulties producing and understanding spoken language. This disorder is typically labeled specific language impairment. Persons diagnosed with specific language impairment (SLI) often have accompanying reading difficulties, but not all children with reading difficulties have specific language impairment.

Current research suggests that many individuals with language learning impairments have a "temporal processing deficit" that can be demonstrated by psychoacoustic measurements of several different types. They have special problems in identifying and therefore correctly sequencing rapidly successive acoustic stimuli because those successive stimuli interfere destructively with one another. This abnormal signal reception is believed to be accounted for by abnormally long integration of acoustic information in the impaired individual's neuronal processing of the sound input stream. On the basis of these findings, procedures have been developed to assess the "temporal threshold" in impaired individuals using a stimulus sequencing task in which pairs of successively presented tonal or vowel-like stimuli were varied in their durations and interstimulus intervals. The temporal threshold is the time separation (interstimulus interval) between two stimuli that are nearby in frequency, and that are of fixed frequency, intensity and duration, at which they can be accurately sequenced by the individual. This method can and has been used as a basis for screening children and adults to identify those with acoustic reception-based language learning problems, and at risk for dyslexia (reading failure).

The abnormal temporal interferences that distinguish the language impaired child appear to underlie the "fuzzy" phonetic reception and "phonological awareness" deficits that also plague them. It has been specifically demonstrated that language impaired children cannot distinguish between specific phonemes (for example, the consonant-vowel contrasts /da/ and /ba/) when the consonant transitions are presented in a fast form, but can identify them if the consonant transition is adequately prolonged in time. This has been interpreted as occurring because in its long form, critical consonant features are represented outside of the domain of destructive interference or integration that destructively alters briefer stimuli.

Studies conducted in animal models and experiments conducted in human subjects performing visual tasks have demonstrated that the correct identification of rapidly successive inputs can be improved markedly with training. On the basis of these new experimental findings and the background perspective on the acoustic reception problems of language impaired individuals described above, a training method was invented to ameliorate the "temporal processing deficits" of language impaired and dyslexic individuals, and to facilitate complex acoustic signal and language processing in general. That training approach is the subject of U.S. patent application Ser. No. 08/351,803, filed Dec. 8, 1994, invented by Tallal et al., entitled, Method and Device for Enhancing the Recognition of Speech Among Speech-Impaired Individuals, which is expressly incorporated herein by this reference. The teachings of that patent application provide a highly effective basis for overcoming, through training, the acoustic sound stream interference problems that limit signal reception in language impaired individuals. With the dramatic "clarification" of speech input that results from such training, children have been found to perform at much higher levels at a wide variety of phonetic reception, speech/language memory, syntactic, semantic, grammatical receptive and expressive language tasks. In general, after training, their language skills are elevated to normal or nearly normal "language quotient" levels.

The particular techniques described in the above-identified patent application focus on the difficulty that SLI persons have in discriminating between a pattern of brief sounds that occur in close temporal proximity to each other. The adaptive training methods taught in that patent application ordinarily involve altering the brief sounds, by prolonging them or increasing their level (intensity), and increasing the interstimulus interval (ISI) between the sounds. These changes in the sounds and in their temporal separation makes them more intelligible to the SLI person. The training program typically involves a regimen of repeated presentation of the modified sounds in a controlled pattern to the SLI individual. The individual is asked to identify the short duration sounds. The ISI between the brief sounds is gradually decreased as the individual's ability to identify the sounds improves. These improvements in the ability of the individual to discriminate between the sounds is monitored throughout the training program. As the perceptual acuity of the person continues to improve, the ISI is decreased even further and the repetition of sounds is repeated with the new ISI. It has been found that, over the course of a training program, an SLI individual's ability to distinguish between brief sounds presented in a rapid sequence may improve significantly. Eventually, as a result of the training, the SLI person may be able to discriminate between substantially unmodified brief sounds, such as consonants, which are temporally separated by an amount typical to a normal speech rate.

While these earlier procedures for the identification and remediation of language perception problems in specific language impaired individuals generally have been highly effective, there exists a need to adopt new procedures consistent with ongoing developments in the understanding of the nature and causes of these perceptual problems. For instance, these earlier treatment methods generally do not consider the potential impact of the ordering of interfering sounds upon the ability of a SLI person to distinguish between the sounds. Additionally, for example, these prior methods do not take into account the possible effects of the spectral content of the interfering sounds upon the ability of a SLI person to differentiate between sounds presented in rapid sequence or simultaneously. Thus, there has been a need to continue to develop improved methods for the identification and treatment of language perception problems in specific language impaired (SLI) individuals based upon other elements of sound patterns such as temporal ordering of the sounds and spectral content of the sounds. The present invention meets this need.

BRIEF DESCRIPTION OF THE DRAWINGS

FIGS. 3, 3A, 3B, 3B-1, 3B-2 and 3C illustrate the flow of a computer program that can control the generation and presentation of the target-mask stimulus patterns.

DETAILED DESCRIPTION OF THE PREFERRED EMBODIMENT

The present invention provides a method, and apparatus for screening individuals for specific language impairment (SLI) and for training individuals who suffer from SLI so as to remediate the effects of the impairment. The novel method and apparatus takes into account both the spectral content of interfering sound stimuli and the temporal ordering (or direction) of the interference between the stimuli. It is well known that even persons with normal language ability may have difficulty detecting a target sound in the presence of masking noise with the same frequency (or spectral) content as the target. Experiments have shown, however, that SLI persons often have greater difficulty than persons with normal language ability in detecting a target sound in the presence of a masking noise with a different spectral content than the target. Moreover, experiments have shown that although the ability of SLI individuals to detect a target sound in the presence of a masking noise improves as the spectral content of the target and the noise are separated by increasing amounts, the ability of non-language impaired persons to detect the target improves at a faster rate as the spectral separation increases. Experiments also have shown that backward masking often is greater in individuals with SLI than in persons who do not experience SLI. Thus, these experiments suggest that SLI persons have lower resolution frequency discrimination than non-SLI persons. Screening according to a presently preferred embodiment of the invention assesses the severity of backward masking interference and the severity of spectral interference in simultaneous and non-simultaneous masking. Training according to the current embodiment aims to reduce the effects of backward masking and spectral interference in persons with SLI.

Screening of an individual for SLI according to a current embodiment of the invention involves presenting the individual with several different patterns of target sound stimuli and mask sound stimuli. A target stimulus is the target of reception. It is the sound signal component to be identified by the individual under test. A target sound stimulus may be a consonant, a tone, a tonal complex, noise, amplitude modulated noise or a frequency sweep, for example. A mask sound stimulus is a sound that may destructively interfere with the target sound stimulus so as to make the target more difficult to detect in the presence of the mask. A mask sound stimulus may be noise with a prescribed spectral content, a tone, a vowel, a word, a word fragment, a sentence, a sentence fragment the sound of many voices in a crowd, a tone, a tonal complex, noise, amplitude modulated noise or a frequency sweep, for example. In the present implementation of the invention, many test patterns comprising different combinations of target and mask sound stimuli are used to assess backward masking effects and spectral interference effects in an individual under test.

Figures 1, 2:
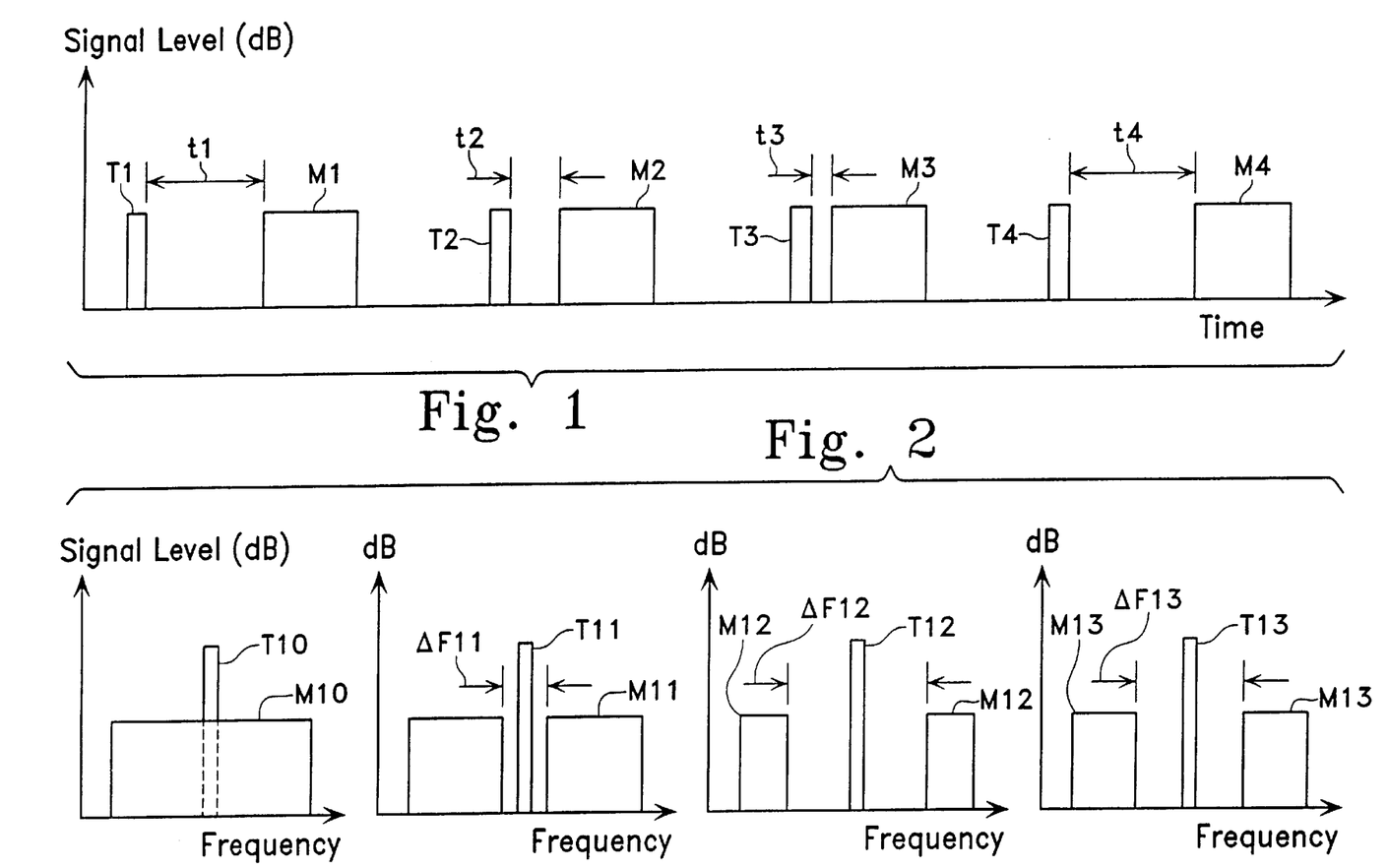
FIG. 1 illustrates an exemplary target-mask sound stimulus pattern which can be used to assess a person for impairment based upon backward masking effects.
FIG. 2 illustrates an exemplary target-mask sound stimulus pattern that may be used to asses spectral masking effects.

Referring to the illustrative drawings of FIG. 1, there is shown an exemplary target-mask sound stimulus pattern which can be used to assess a person for impairment based upon backward masking effects. A series of target-mask stimuli pairs are provided in which individual target stimuli and corresponding mask stimuli are temporally sequenced with the target preceding the corresponding mask. The exemplary pattern includes the target-mask pair T4–M4, in which the target sound stimulus T4 precedes the mask sound stimulus M4. The pattern also includes target-mask pairs, T1–M1, T2–M2 and T3–M3. It will be appreciated that only a few representative target-mask pairs are shown, and that there ordinarily will be many more target-mask pairs in a typical pattern in accordance with the invention. The time interval between target-mask pairs varies. For example, the time interval t4 between T4 and M4 is greater than the time interval t3 in T3–M3 or the time interval t1 in T1–M1. Moreover, the time interval t3 is shorter than the time intervals t4, t2, or t1. In general, the shorter the duration of the target the more pronounced the masking effect. Target durations ranging from almost 0 milliseconds (msc) to about 500 msc generally are employed in the screening and training in accordance with the invention. An individual under test is expected to indicate when he or she perceives a target stimulus. An electronic record is created which records the individual's responses to the various target-mask pairs in the test pattern. The record which may be encoded in electronic media provides a map of the individual's ability to discern target sound stimuli as a function of the temporal spacing between a target sound stimulus and a backward mask sound stimulus.

Referring to the illustrative drawings of FIG. 2, there is shown an exemplary target-mask sound stimulus pattern that may be used to assess spectral masking effects according to the invention. A series of target-mask stimuli pairs are provided in which individual target stimuli and corresponding mask stimuli occur simultaneously (or overlap in time) and in which the spectral content of the mask varies. For example, mask M10 lacks a frequency notch. In other words, mask M10 is continuous throughout the range of frequencies provided within M10. Consequently, mask M10 contains frequency components that overlap the frequencies in the target T10. See, Patterson, Roy D., "Auditory Filter Shapes Derived With Noise Stimuli", Journal of the Acoustical Society of America, Volume 59, No. 3, pp. 640–654. In contrast, mask M11 has a spectral notch with a width of delta F11; mask F12 has a spectral notch of delta F12; and mask has a frequency notch of delta F13. It will be appreciated from the illustrative drawings of FIG. 2 that the width of the spectral notch in M12 is greater than the widths of spectral notches in M11 or M13, and that the width of the spectral notch in M11 is narrower than the width of the spectral notch in M13. Ordinarily, the wider the frequency notch the easier it will be to detect the target in the presence of the mask. In a presently preferred embodiment frequency (or spectral)

notches of 0, 0.2/(target tone frequency), 0.4/(target tone frequency) and 0.8/(target tone frequency) are employed. An individual under test is expected to indicate when he or she perceives a target stimulus in the presence of each of these separate masks. More specifically, the target sound stimulus intensity level at which the individual detects the target T10 in the presence of mask M10 is determined. The target sound stimulus intensity level at which the individual detects the target T11 in the presence of mask M11 is determined. The target sound stimulus intensity level at which the individual detects the target T12 in the presence of mask M12 is determined. The target sound stimulus intensity level at which the individual detects the target T13 in the presence of mask M13 is determined. See Rosen, Stuart and Baker, Richard J., "Characterizing Auditory Filter Nonlinearity", Hearing Research, volume 73, 1994, pp.231–243. An electronic record is created which records the individual's responses to the various target-mask pairs in the test pattern. The record which may be encoded in electronic media provides a map of the individual's ability to discern target sound stimuli as a function of spectral interference between a target sound stimulus and a mask sound stimulus.

The different target-mask sound stimulus patterns in FIGS. 1 and 2 are used to screen for two distinct problems in auditory perception. Target-mask patterns of the general type shown in FIG. 1 in which the interstimulus interval is varied in a backward masking setting are particularly helpful in evaluating the degree to which an individual is unable to detect a target sound stimulus due to backward masking effects. Usually, the greater the backward masking effect experienced by a person, the wider the time interval must be between target and mask before the person can detect the target in the presence of the following mask. Alternatively, the greater the backward mask effect, the louder the target stimulus must be in order to be detectable in the presence of the backward mask stimulus. Mask patterns of the general type shown in FIG. 2 in which the width of a spectral notch is varied are especially useful in assessing the impact of spectral interference upon an individual's ability to detect a target sound stimulus. Typically, the greater the spectral interference experienced by a person, the wider the spectral notch must be between target and mask before the person can detect the target in the presence of the mask. Therefore, varying the spectrum of the mask can reveal the severity of both simultaneous (overlapping) and non-simultaneous (backward or forward) mask effects. Thus, the exemplary target-mask sound stimulus patterns of FIGS. 1 and 2 are used to evaluate two independent auditory perceptual correlants.

There are significant advantages in screening individuals for SLI in accordance with the present invention. For example, research shows that SLI individuals often experience more severe backward masking effects than the normal (or non-SLI) population. Hence, the target-mask patterns exemplified in FIG. 1 can be especially useful in identifying persons likely to suffer from SLI. Research also shows that SLI persons often experience greater difficulty than the normal (or non-SLI) population in detecting a target sound stimulus in the presence of a mask sound stimulus when the target and mask possess different spectral content. Thus, the target-mask patterns exemplified in FIG. 2 can be particularly useful in determining the extent of both simultaneous and non-simultaneous masking in SLI persons.

It will be appreciated that in backward masking, varying the spectral content of the mask can be used to ascertain the severity of the backward mask problem. For instance, a series of target-mask pairs can be provided in which the target is presented before the mask (backward mask scenario); a spectal notch in the mask is varied throughout the pattern while ISI is fixed; and, for each different spectral notch, a determination is made as to the threshold target stimulus level at which an individual can detect the target. In this manner a map of an individual's ability to detect a target in the presence of backward masks having different spectral content can be created.

Assessment of spectral interference in both non-simultaneous and simultaneous masking are important to develop a more complete understanding of the basis for an SLI person's language impairment. For example, backward masking, a form of non-simultaneous masking, is believed to be an underlying cause of masking of a consonant sound by a following vowel sound. In the fragment /ba/, for instance, it is believed that the consonant /b/ in some cases may be backward masked by the vowel /a/. In contrast, for example, simultaneous masking, in which the target and mask overlap in time, is believed to be an underlying problem in differentiating sounds that are similar or overlapping in spectral content. The short /i/ and the short /a/ sounds, for instance, sometimes may interfere with each other due to simultaneous masking effects. See Stark, Rachel E. and Heinz, John m., "Vowel Perception in Children with and Without Language Impairment", Journal of Hearing and Speech Research, Volume 39, pp.860–869. Of course, a better understanding of the nature of a person's learning impairment may result in the development of an improved and more realistic course of adaptive training for such individual.

EXAMPLE

The following example reports the results of psychophysical tests employing simple tones and noises showing that children with specific language impairment have severe auditory perceptual deficits for brief but not long tones in. particular sound contexts. The data supports the view that language difficulties result from problems in auditory perception, and provide further information about the nature of these perceptual problems.

Figure 1A:
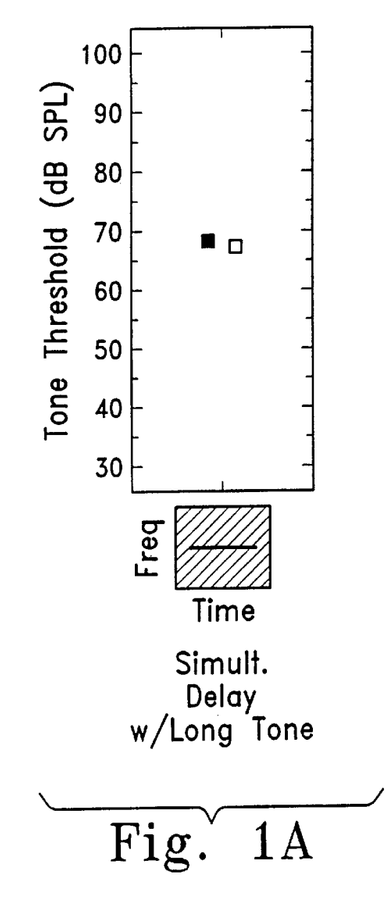
FIG. 1A shows results indicating tone level required for subjects to detect long tone in the exemplary masking condition.
Figure 1B:
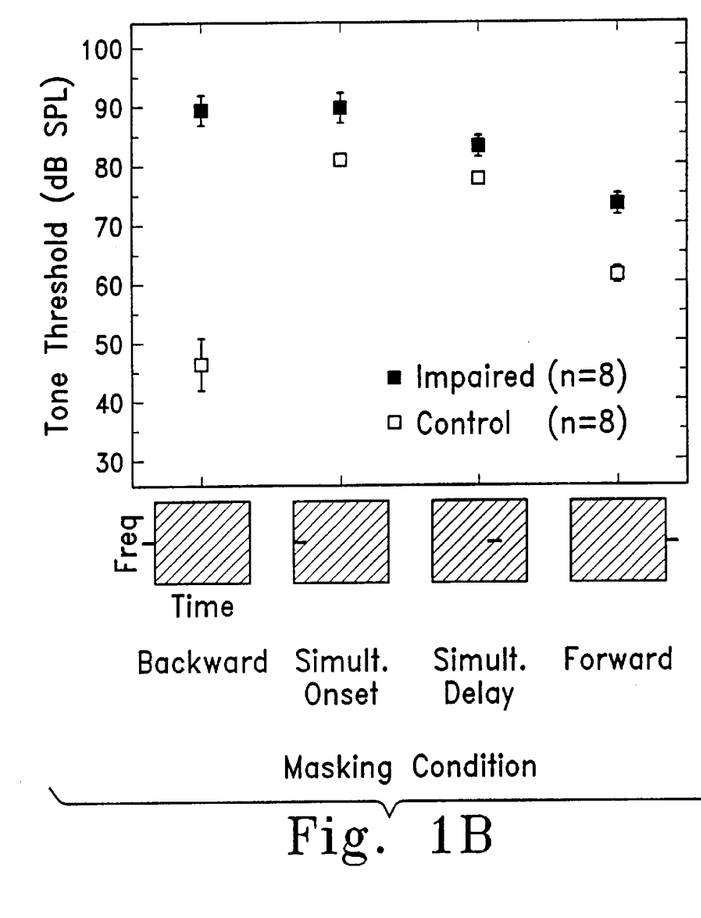
FIG. 1B results for the same subjects indicating the detection threshold for a brief tone presented with the bandpass noise at each of four temporal positions illustrated schematically along the abscissa.
Figure 2A:
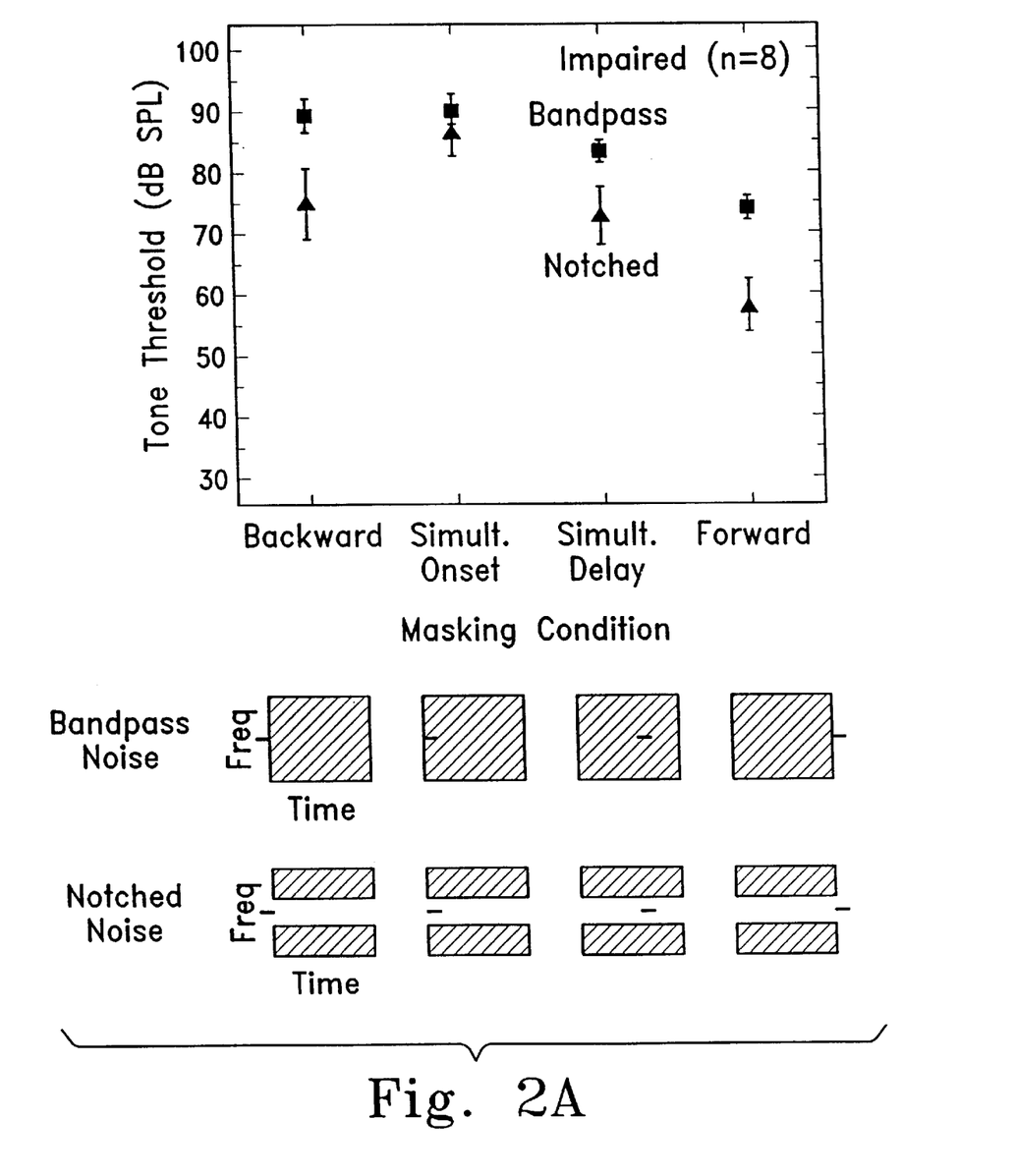
FIGS. 2A and 2B show the mean tone thresholds for both the bandpass and notched noises.
Figure 2B:
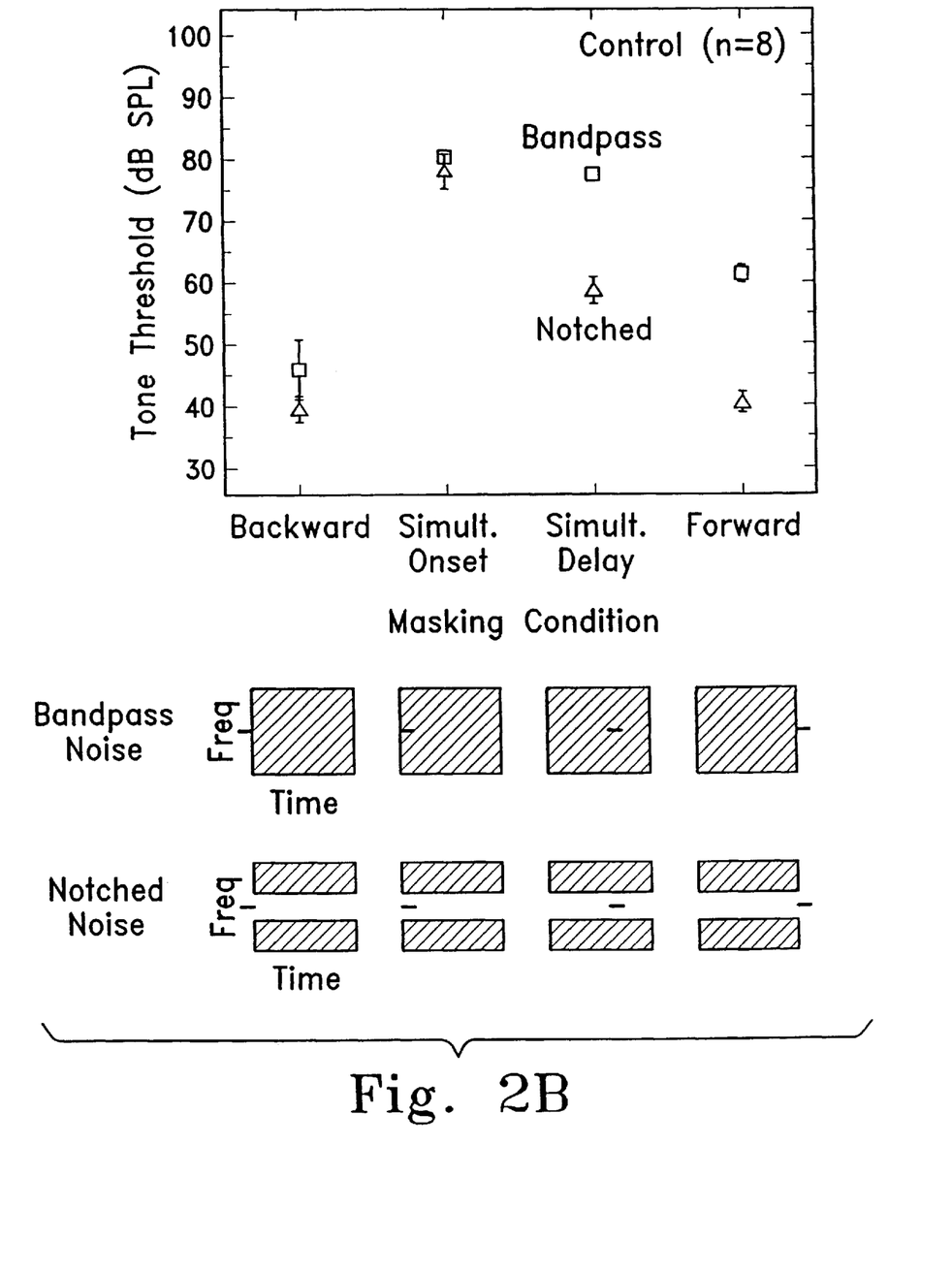
Figure 3:
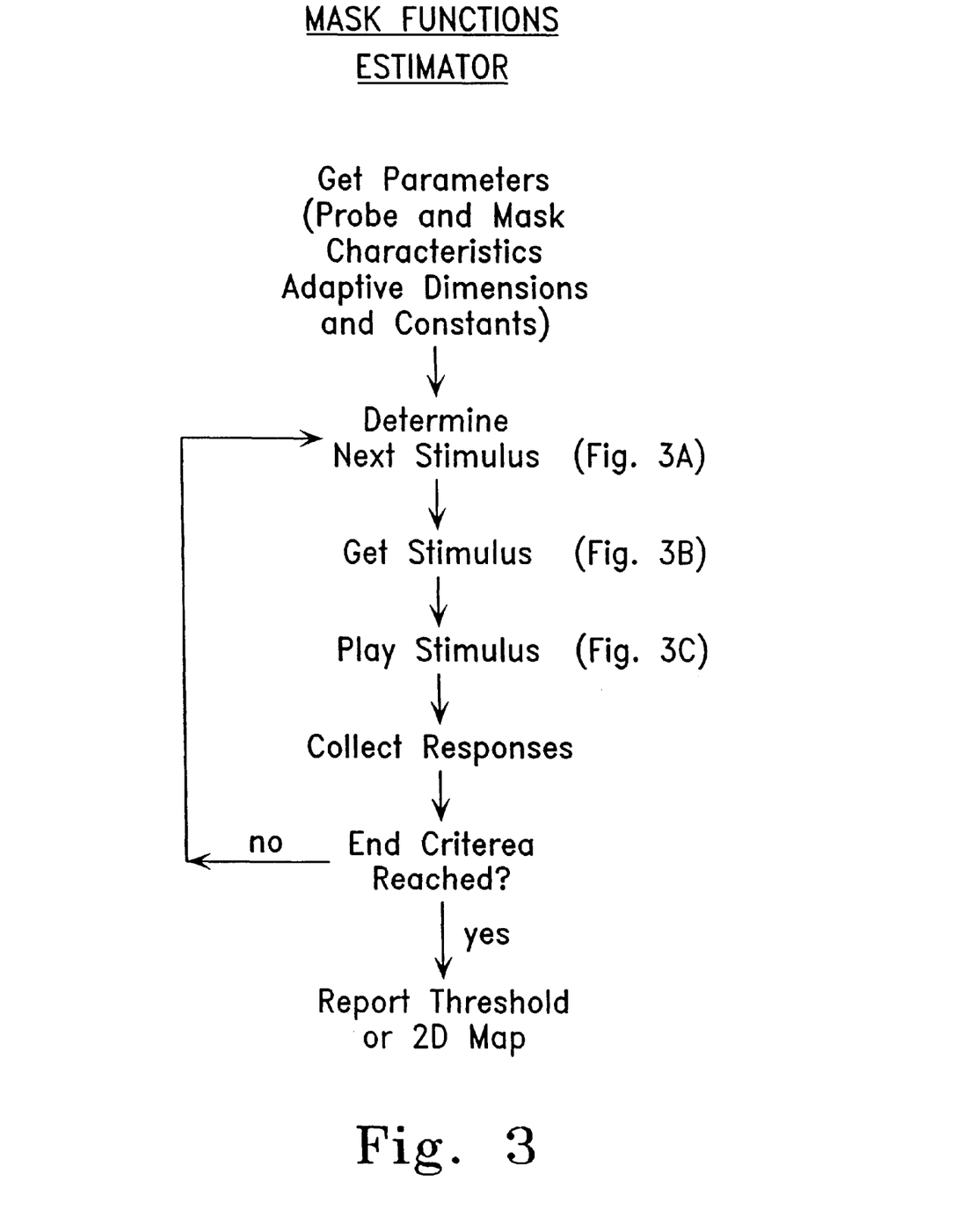
Figure 3A:
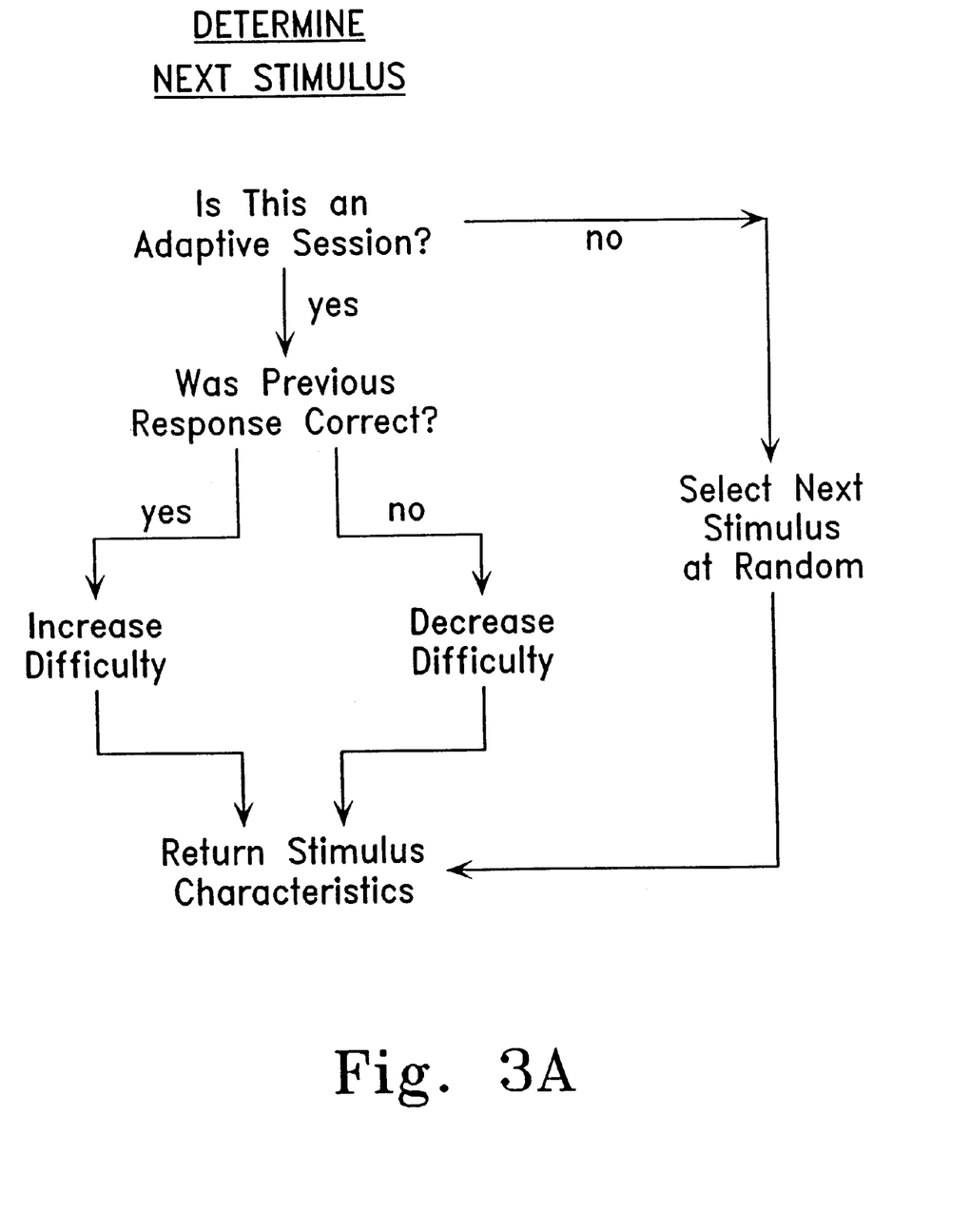
Figure 3B:
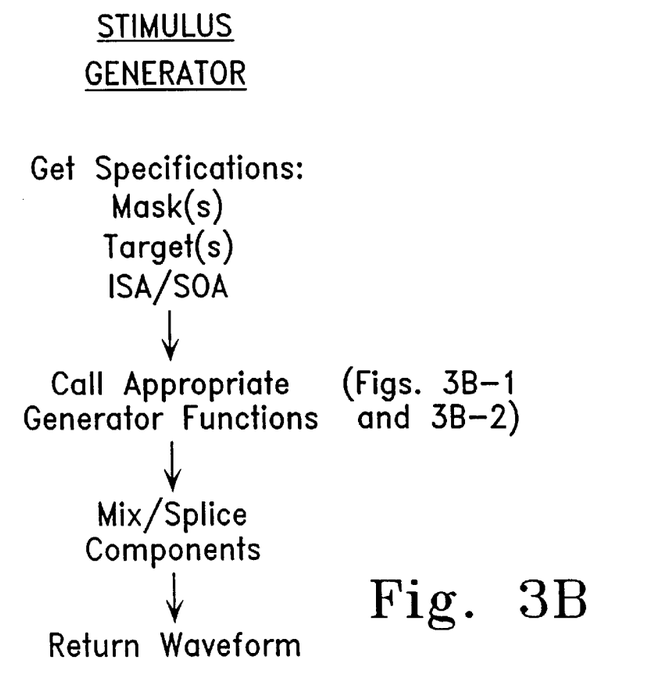
Figure 3B:
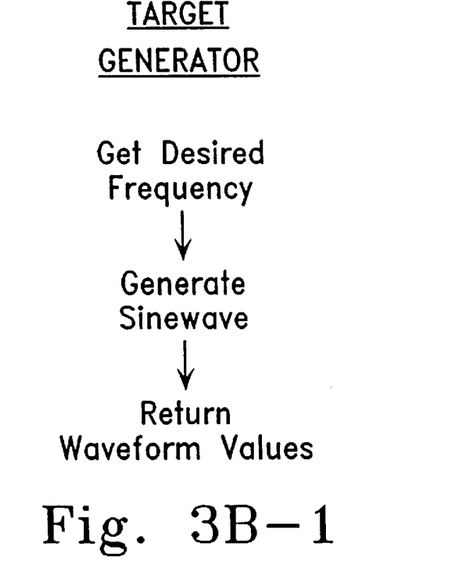
Figure 3B:
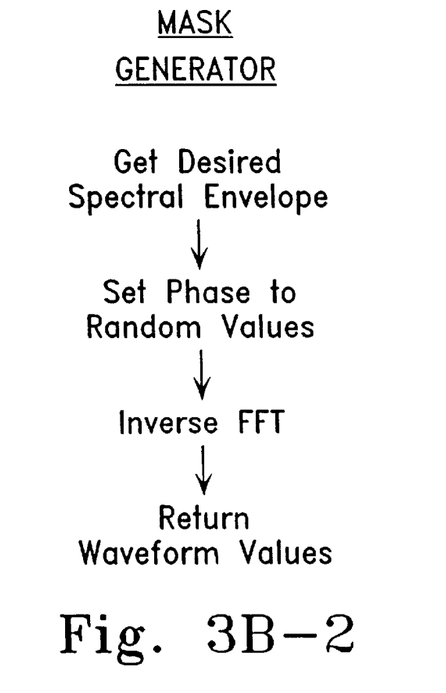
Figure 3C:
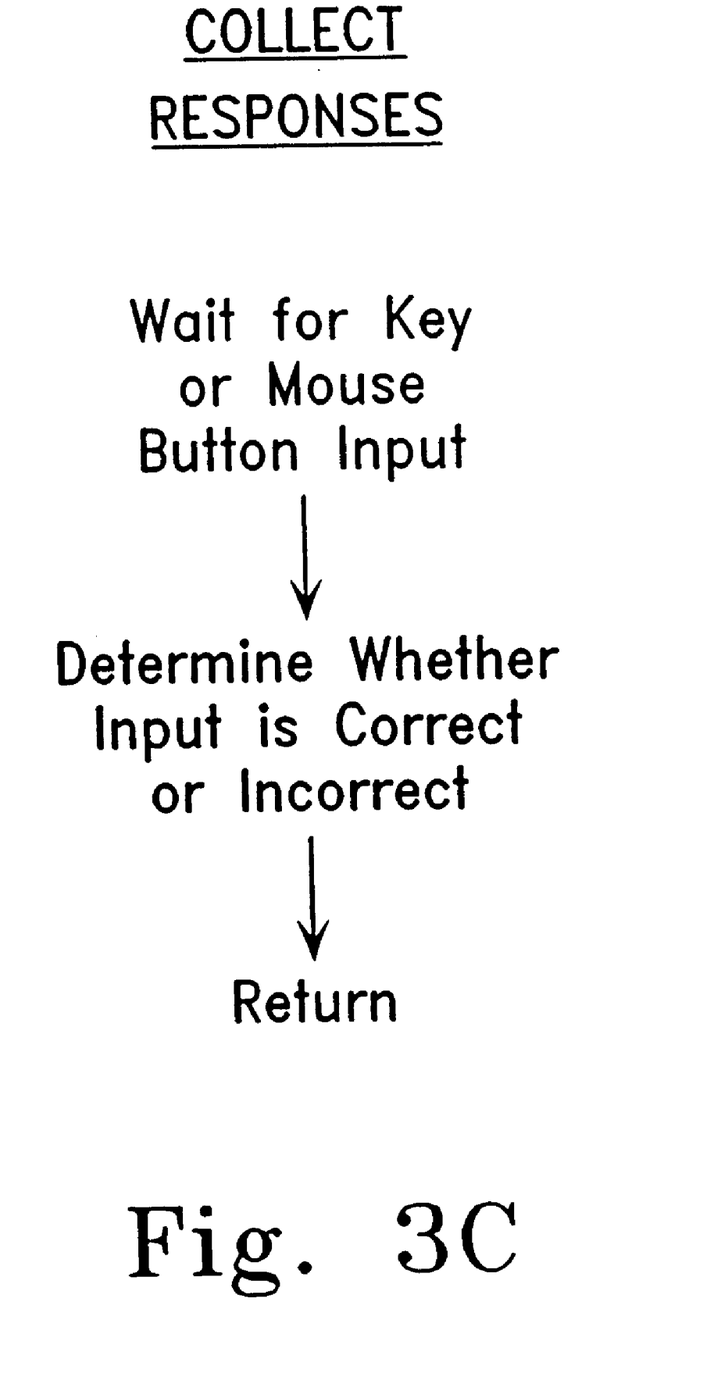

FIG. 1: Average tone level required by 8 language-impaired (filled squares) and 8 control (open squares) children to just detect a long tone temporally centered in a bandpass noise (panel A), or a brief tone presented before, during or after that noise (panel B). The error bars indicate plus and minus one standard error of the mean across subjects. The stimuli are illustrated schematically along the abscissa.

FIG. 2: Average tone level required by 8 language-impaired (panel A) and 8 control (panel B) children to just detect a brief tone presented before, during or after a bandpass (squares, replotted from FIG. 1B) or notched (triangles) noise. The error bars indicate plus and minus one standard error of the mean across subjects. The stimuli are illustrated schematically at the bottom of the figure.

We measured the detection threshold for a brief tone presented before, during or after two different masking noises in 8 children diagnosed with specific language impairment, and in 8 control children with normal language skills who matched the others in age and nonverbal intelligence. Details of the two groups are provided in Table 1. Before beginning the tests with the brief tones, we introduced the children to the listening task by measuring their detection thresholds for a long tone presented in the temporal center of a "bandpass" noise that included frequencies at and near the tone frequency. The points above the schematic illustration of the stimuli in FIG. 1A show that the same mean tone level was required by specifically language impaired (filled squares) and control (open squares) children to detect the long tone in this masking condition [$F(1,14) < 1 p > 0.05$].

FIG. 1B shows the results of our subsequent measurements in the same children of the detection threshold for a brief tone presented with the bandpass noise at each of four temporal positions illustrated schematically along the abscissa. The performance pattern of control children (open squares) was just as expected based on previous work on normal auditory masking: The tone was easier to detect when it was presented just before or just after, as opposed to during, the noise, and was easiest to detect when it preceded rather then followed the noise. In comparison to controls, children with specific language impairment (filled squares) needed a higher tone level for detection in every condition. Most remarkably, impaired children had as much or more difficulty detecting the tone when it was presented before the noise (the backward-masking condition) as when it was presented during or after the noise. There was no overlap in performance between the two groups in the backward-masking condition.

We also measured detection thresholds in the same children for a brief tone presented at each of the four temporal positions in a spectrally "notched" noise that excluded frequencies at and near the tone frequency. The two panels of FIG. 2 show the mean tone thresholds for each group for both the bandpass (squares; replotted from FIG. 1B) and notched (triangles) noises. The conditions are schematically illustrated at the bottom of the figure. For both impaired and control children, the tone was typically easier to detect with the notched than with the bandpass noise. This is expected in normal hearing. However, in contrast to most adults, neither group of children showed a clear threshold difference between the two masker types when the tone and noise started simultaneously.

Two aspects of the performance of impaired children with the notched noise are particularly important. First, language-impaired children were better at hearing the tone presented before (the backward-masking condition) the notched than the bandpass noise. Their severe perceptual deficit for tones presented in this temporal position was worst when the tone and following noise had similar frequencies. Follow-up tests on 4 additional impaired children showed that the detection threshold in the backward masking condition reached control values when the spectral notch in the masker was made sufficiently wide. Thus, impaired children had perceptual difficulties in certain temporal and spectral sound contexts, but did not display a general deficit in the perception of rapidly presented sounds. Second, the mean threshold difference between the notched and bandpass noises was smaller for impaired than for control children in both the simultaneous-delay (10.5 dB vs. 18.6 dB) and forward (15.7 dB vs. 20.5 dB) masking conditions. This indicates that impaired children were less able than controls to take advantage of a frequency separation between the tone and noise to aid detection of the tone.

A 2×2×4 analysis of variance performed on the data in FIG. 2 revealed significant main effects for subject group [$F(1,112) = 102.70, p<0.0001$], noise type [$F(1,112) = 43.94, p<0.0001$], and tone position [$F(3,112) = 41.93, p<0.0001$]. There were also significant interactions between subject group and tone position [$F(3,112) = 16.72, p<0.000$] and noise type and tone position [$F(3,112) = 3.53, p = 017$], but not between the subject group and the noise type [$F(1,112) = 0.08, p>0.05$], nor among the three factors [$F(3,112) = 1.07, p>0.05$]. A Scheffe post hoc analysis indicated that the thresholds of the two subject groups differed significantly only in the two backward-masking conditions ($p<0.0001$ for the bandpass masker and $p = 0.0002$ for the notched-noise masker).

In sum, these results suggest that children with specific language impairment are severely impaired in their ability to (1) separate a brief sound from a rapidly following sound of similar frequency, and (2) enhance the detection of a brief tone by exploiting a frequency difference between the tone and a longer co-occurring or preceding masking sound. These auditory perceptual deficits could clearly degrade the perception of the brief acoustic elements of speech. Many individuals with language impairment and other disorders related to spoken language might benefit from diagnoses incorporating the auditory tests used here, and from auditory training that focuses on their most severely impaired abilities. The present auditory tests might also aid in the diagnosis and treatment of persons with reading difficulties. We have preliminary data on 12 such individuals. Five had excessive amounts of auditory backward masking, but none had as much masking as the children with specific language impairment. Our results are in accord with the conclusion of a recent review that some, but not all, children with reading problems have difficulties accurately perceiving rapidly presented stimuli. Our data are also consistent with a previous report showing that children with reading difficulties are particularly poor at discriminating words that differ only in their first sound. Finally, the temporal and spectral specificity of the auditory perceptual deficits reported here may serve to guide the search for the underlying neural bases of language disorders.

Methods

Stimuli: All stimuli were generated digitally. Tone: 1000 Hz, 20 or 200 ms onset-to-offset. Noises: 600–1400 Hz (bandpass noise) or 400–800 Hz and 1200–1600 Hz (notched noise), 300 ms onset-to-offset, 40 dB SPL spectrum level. Gating envelope: 10-ms cosine squared for all stimuli. Masking conditions: The 20-ms tone was turned on at four different times defined relative to the onset of the 300-ms noise: -20 ms (backward masking), 0 ms (simultaneous-onset masking), 200 ms (simultaneous-delay masking), or 300 ms (forward masking). The 200-ms tone was turned on 50 ms after noise onset.

Procedure: We used a standard, adaptive, two-interval forced-choice procedure to estimate the tone level required for 94% correct detections. The observation intervals were separated by 800 ms. Visual displays on a computer screen marked the observation intervals and gave feedback. Each reported brief-tone threshold was based on the mean of two or three 30-trial measurements per child. Three measurements were always collected, but the most deviant estimate was omitted if the standard deviation of the three was greater than 15 dB. The average within-subject standard error was 3.7 dB for impaired children and 2.5 dB for control children. Because the long-tone condition was used to acquaint the children with the task, we report only the last threshold estimate of the one to three obtained from each child in that condition; in total, the 8 impaired children completed 14 threshold estimates and the 8 control children 13 estimates in the long-tone condition. We collected the data with the long tone first, and then presented the four brief-tone conditions in pairs [bandpass then notched noise] in a diagram balanced latin square. We tested each child individually in a sound-attenuated room. Stimuli were delivered to the right ear over Sennheiser HD450 headphones. All children were paid for their participation.

TABLE 1

|  | Language Impaired MEAN (sd) | Control |
|---|---|---|
| Age | 8.1 (6.3) | 8.0 (7.1) |
| Sex | 6 M,2 F | 3 M, 5 F |
| TONI-2 | 101 (5.3) | 105.1 (6.5) |
| CELF-R: |  |  |
| Receptive Language | 83.4 (6.9)+ | 112.5 (7.8) |
| Linguistic Concepts | 7.4 (1.5)+ | 10.6 (2.3) |
| Sentence Structure | 6.9 (1.6) | 12.4 (2.0) |
| Oral Directions | 7.5 (2.1) | 13.0 (2.1) |
| Expressive Language | 70.7 (4.8)+ | 98.1 (5.2) |
| Word Structure | 5.5 (1.6) | 8.8 (1.6) |
| Formulated Sentences | 4.9 (1.3) | 8.6 (1.1) |
| Recalling Sentences | 6.3 (2.1) | 12.0 (1.3) |
| Total Language 75.3 (4.5)+ | 105.3 (5.4) |  |

Table 1: Mean of the standard scores on the Test of Nonverbal Intelligence (TONI-2)[25] and the Clinical Evaluation of Language Fundamentals-Revised (CELF-R)[26] for the 8 specifically language impaired (middle column) and 8 control (right column) children. The mean age (years.months) and sex distribution of both groups is also provided. The standard deviation of each mean value is shown in parentheses. Plus signs indicate values based on the mean of 7 of the 8 impaired children due to missing test results.

Apparatus Set Up and Screening Maps

Figure 4A:
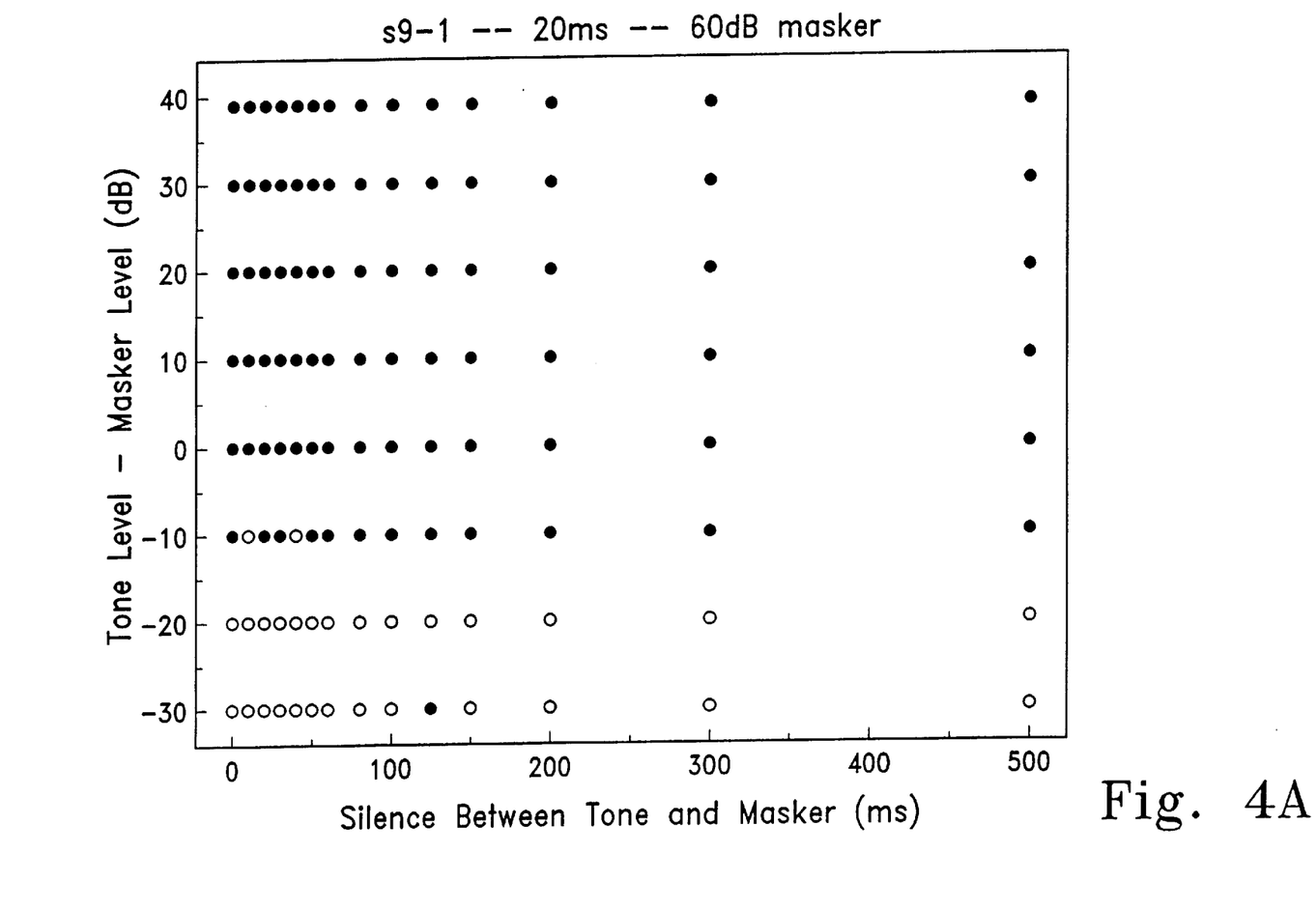
FIGS. 4A–4C illustrate two dimensional mappings of three different individuals tested for the ability to detect a target in a backward masking situation with a 20 msc target length and without a spectal notch in the mask. The map of FIG. 4A represents result for a normal, non-language impaired person. The map of FIG. 4B represents results for a midly language impaired person. The map of FIG. 4C represents results for a severely language impaired person.
Figure 4B:
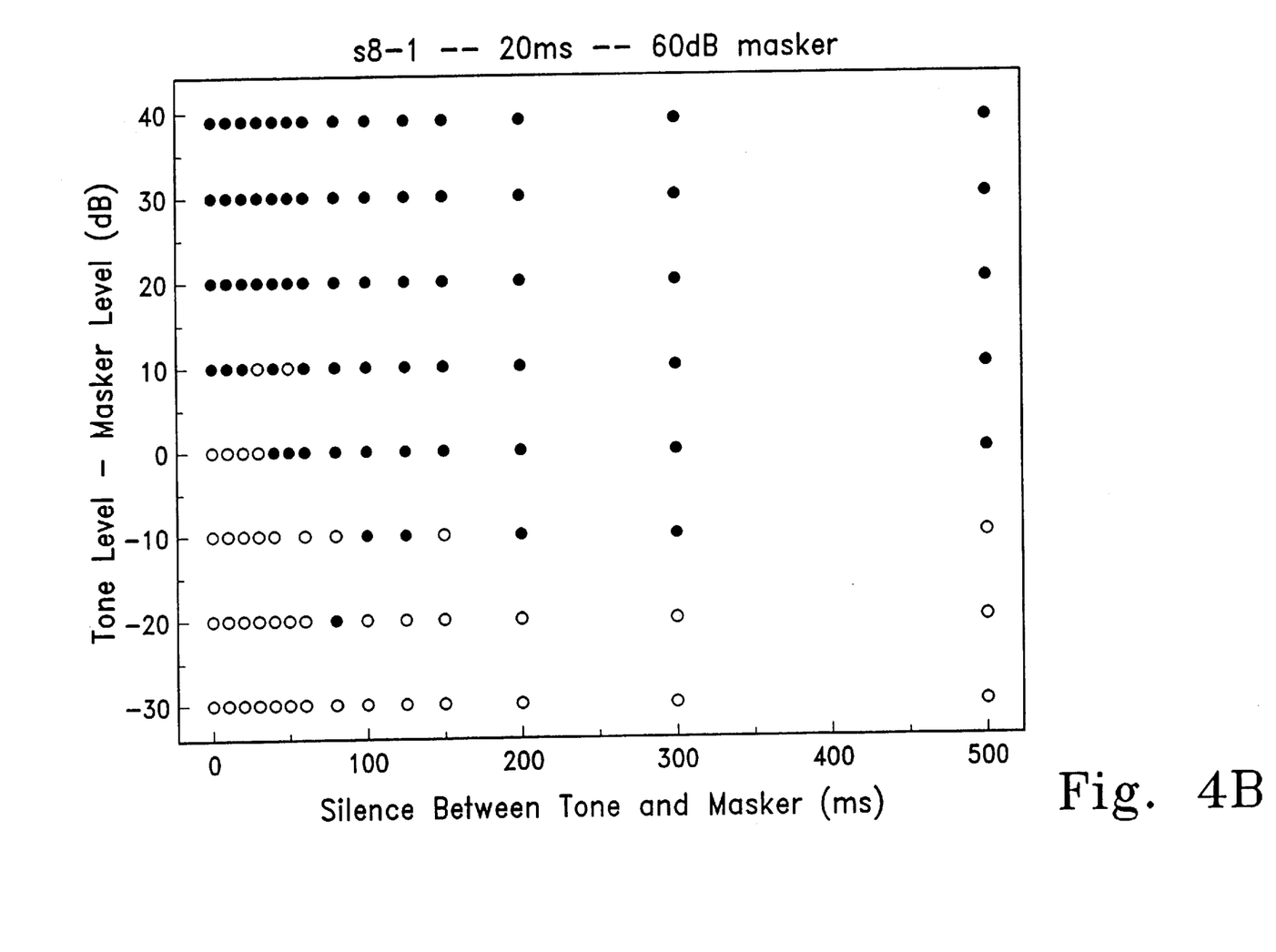
Figure 4C:
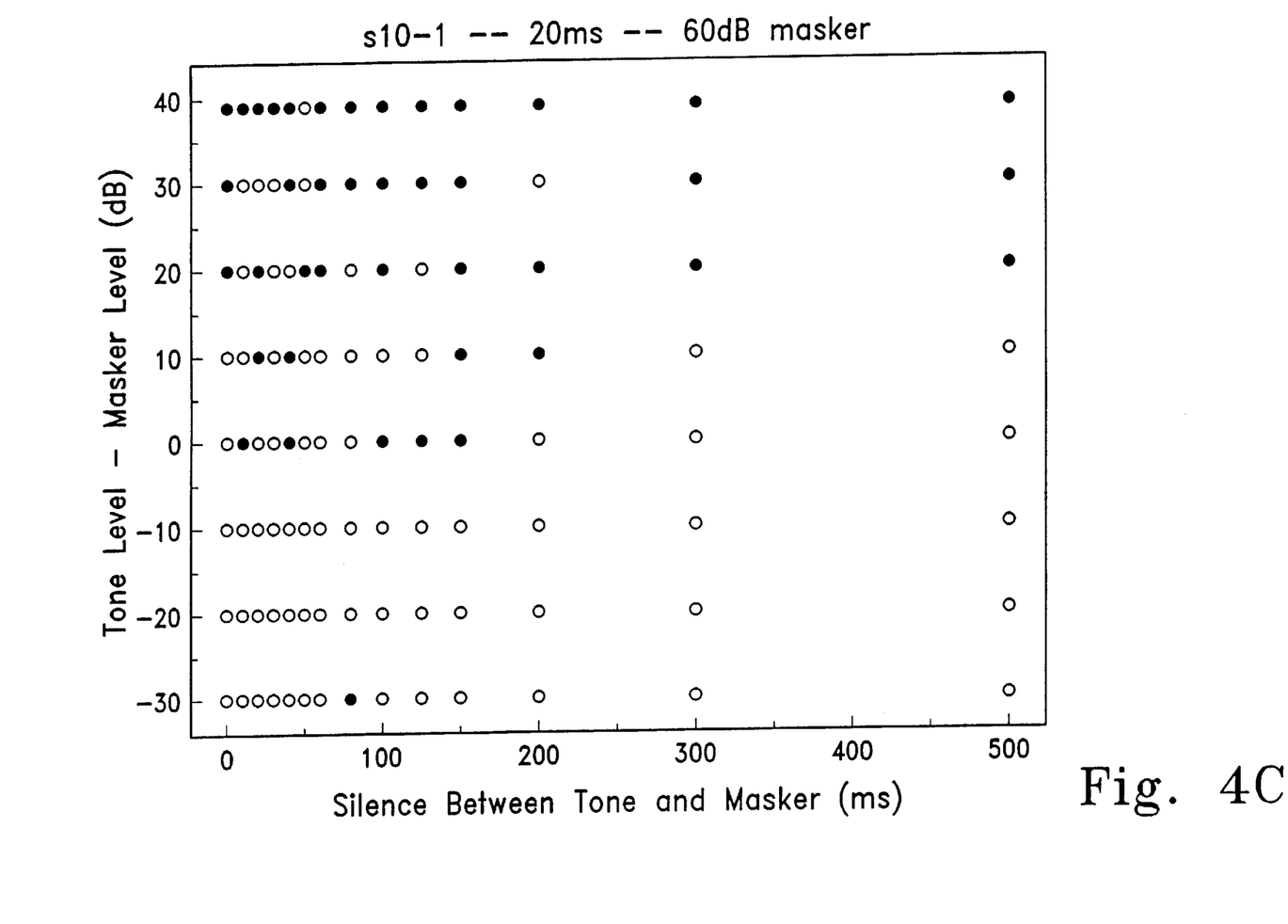

Screening and training in accordance with the present invention can be performed using a standard personal computer equipped with an input device such as a keyboard or a mouse and headphones to deliver pattern of target-mask pairs to an individual. Conventional signal generation equipment can be used to actually generate the target-mask patterns. The illustrative drawing of FIGS. 3 and 3A–3C describe the flow of a computer program that can control the generation and presentation of the target-mask stimulus patterns. The illustrative drawings of FIGS. 4A–4C are two dimensional mappings of three different individuals tested in accordance with the invention for the ability to detect a target in a backward masking situation with a 20 msc target length and without a spectal notch in the mask. The filled circles represent data points (mask level and ISI) for which the person under test could detect the target. At a tone level of 0, the target has the same intensity as the mask. The map of FIG. 4A represents result for a normal, non-language impaired person. The map of FIG. 4B represents results for a mildly language impaired person. The map of FIG. 4C represents results for a severely language impaired person.

What is claimed is:

1. A method of screening an individual for audio perception problems, the method comprising the steps of: providing multiple respective target-mask sound stimuli combinations in which the target has a prescribed frequency and the mask has a spectral notch at about the prescribed frequency, the combinations including, the target occurrence before the mask, the target occurrence during the mask and the target occurrence after the mask; determining, for each target-mask combination, the relative target level at which the individual can detect the target sound. stimulus.

2. The method of claim 1 including the further step of: changing the interstimulus interval (ISI) between the target and the mask in at least one of the combinations; and repeating the steps of providing and determining with the changed ISI.

3. The method of claim 1 including the further step of: changing the length of the target sound stimulus in at least one of the target-mask combinations; and repeating the steps of providing and determining with the changed target sound stimulus length.

4. The method of claim 3 wherein said step of changing involves prolonging the target sound stimulus in at least one of the target-mask combinations.

5. A method of screening an individual for audio perception problems, the method comprising the steps of:
   a) selecting a target sound stimulus having a prescribed frequency;
   b) selecting a mask sound stimulus with a spectral notch at about the prescribed frequency of the target sound stimulus;
   c) changing the spectral notch by a prescribed amount;
   d) providing a target-mask sound stimuli combination in which the target has the prescribed frequency and the mask has the changed spectral notch;
   e) determining whether the individual can detect the provided target sound stimulus in the presence of the mask with the changed spectral notch; and
   f) repeating the steps c) through e) for a prescribed collection of target-mask sound stimuli combinations.

6. The method of claim 5 including the further step of recording the results of said step of determining in electronic media.

7. The method of claim 5 wherein said step of changing the spectral notch involves narrowing the spectral notch.

8. The method of claim 5 wherein said step of changing the spectral notch involves widening the spectral notch.

9. The method of claim 5 wherein said step of providing a target-mask combination involves providing the target sound stimulus before the mask sound stimulus.

10. The method of claim 5 wherein said step of providing a target-mask combination involves providing the target sound stimulus during the mask sound stimulus.

11. The method of claim 5 wherein said step of providing a target-mask combination involves providing the target sound stimulus and the mask sound stimulus with simultaneous onset.

12. The method of claim 5 wherein said step of providing a target-mask combination involves providing the target sound stimulus after the mask sound stimulus.

13. The method of claim 5 including the further steps of: changing the interstimulus interval (ISI) between the target and the mask; and repeating said steps of providing and determining with the changed ISL.

14. The method of claim 5 including the further steps of: changing the length of the target sound stimulus in at least one of the target-mask combinations; and repeating said steps of providing and determining with the changed target sound stimulus length.

15. The method of claim 14 wherein said step of changing involves prolonging the target sound stimulus of the target sound stimulus.

16. A method of screening individuals for audio perception problems, the method comprising the steps of:
   a) selecting a target sound stimulus having a prescribed frequency;
   b) selecting a mask sound stimulus with a spectral notch at about the prescribed frequency of the target sound stimulus;
   c) changing the spectral notch by a prescribed amount;
   d) providing multiple respective target-mask sound stimuli
   e) combinations in which the target has the prescribed frequency and the mask has the changed spectral notch, the combinations including, the target occurrence before the mask, the target occurrence during the mask and the target occurrence after the mask;
   f) for each target-mask combination, determining the relative target level at which the individual can detect the target sound stimulus; and
   g) repeating the steps c) through e) for a prescribed collection of target-mask sound stimuli combinations.

17. The method of claim 16 including, after step e) and before step f), the further step of:
   a) e1) changing the interstimulus interval (ISI) between the target and the mask in at least one of the target-mask combinations; and wherein said step f) includes repeating steps c), d), e) and e1) for a prescribed collection of target-mask sound stimuli combinations and ISIs.

18. The method of claim 17 including, after step e) and before step f), the further step of:
   a) e1) changing the length of the target sound stimulus in at least one of the target-mask combinations; and wherein said step f) includes repeating steps c), d), e) and e1) for a prescribed collection of target-mask sound stimuli combinations and changed target sound stimulus lengths.

19. The method of claim 18 wherein said step e1) involves prolonging the target sound stimulus of the target sound stimulus.

* * * * *